United States Patent
Rollins et al.

(10) Patent No.: US 7,314,112 B1
(45) Date of Patent: *Jan. 1, 2008

(54) METHOD AND DEVICE FOR UTILIZATION OF A STETHOSCOPE AS A NEUROLOGICAL DIAGNOSTIC TOOL AND PERCUSSION TOOL

(76) Inventors: Aaron Rollins, 220 W. 26 th St., Suite 705, New York, NY (US) 10001; Tor Alden, 32 Granville Way, Basking Ridge, NJ (US) 07920

( * ) Notice: Subject to any disclaimer, the term of this patent is extended or adjusted under 35 U.S.C. 154(b) by 239 days.

This patent is subject to a terminal disclaimer.

(21) Appl. No.: 11/181,645

(22) Filed: Jul. 14, 2005

Related U.S. Application Data

(63) Continuation-in-part of application No. 10/608,385, filed on Jun. 27, 2003, now Pat. No. 6,966,400.

(60) Provisional application No. 60/392,319, filed on Jun. 27, 2002.

(51) Int. Cl.
*A61B 7/02* (2006.01)
*A61B 5/02* (2006.01)

(52) U.S. Cl. ........................ 181/131; 600/528

(58) Field of Classification Search ................ 181/131, 181/126, 130; 600/528; D24/134; 381/67; 128/864
See application file for complete search history.

(56) References Cited

U.S. PATENT DOCUMENTS

| | | | | |
|---|---|---|---|---|
| 2,515,471 A | * | 7/1950 | Ratzan | 181/131 |
| 2,566,687 A | * | 9/1951 | Wehby | 600/202 |
| 2,807,328 A | * | 9/1957 | Gould | 181/131 |
| 2,858,898 A | * | 11/1958 | Cinquini | 181/137 |
| 3,316,998 A | * | 5/1967 | Krug | 181/137 |
| 4,239,089 A | * | 12/1980 | Nelson | 181/131 |
| 4,324,261 A | * | 4/1982 | Mark et al. | 600/553 |
| 4,643,195 A | * | 2/1987 | Friedman | 600/553 |
| 5,910,992 A | * | 6/1999 | Ho | 381/67 |
| 5,989,186 A | * | 11/1999 | Alatriste | 600/200 |
| 6,454,045 B1 | * | 9/2002 | Ryan | 181/131 |
| 6,510,918 B2 | * | 1/2003 | Bates | 181/131 |
| 6,790,184 B2 | * | 9/2004 | Thierman | 600/553 |
| 6,932,186 B2 | * | 8/2005 | Costa et al. | 181/131 |
| 6,966,400 B1 | * | 11/2005 | Rollins et al. | 181/131 |

FOREIGN PATENT DOCUMENTS

EP       269048  A1  *  6/1988

* cited by examiner

*Primary Examiner*—Edgardo San Martin
(74) *Attorney, Agent, or Firm*—Benjamin Appelbaum

(57) ABSTRACT

A tool for neurological and diagnostic testing comprises the combination of a stethoscope with a reflex hammer including a light. When mounted on the stethoscope head the reflex hammer extends beyond the head, without interfering with the normal use of the stethoscope. A handle, which may or may not be joined to the reflex hammer, is positioned on the flexible stethoscope tubing and provides a gripping surface for using the tool for neurological testing. One embodiment includes a light within the reflex hammer, so that a light is available for testing responses to light at the same time as checking other responses. The reflex hammer and light combination is adaptable for use with binaural and electronic stethoscopes, thus providing a convenient set of instruments within a single device. A detent on the handle provides an ergonomic grip, or a place for inclusion of indicia.

22 Claims, 14 Drawing Sheets

METHOD AND DEVICE FOR UTILIZATION OF A STETHOSCOPE AS A NEUROLOGICAL DIAGNOSTIC TOOL AND PERCUSSION TOOL

CROSS-REFERENCE TO RELATED APPLICATIONS

This application is a continuation-in-part of U.S. patent application Ser. No. 10/608,385, filed 27 Jun. 2003, now U.S. Pat. No. 6,996,400, which application claims the benefit of U.S. Provisional Patent Application Ser. No. 60/392,319, filed 27 Jun. 2002, the contents of which are hereby incorporated by reference herein in their entirety.

FIELD OF THE INVENTION

This invention relates to a medical diagnostic tool, and more specifically to a stethoscope capable of neurological diagnosis, percussion functions and responses to light.

BACKGROUND OF THE INVENTION

Reflex hammers, which have heretofore been in common use, have had a variety of functional limitations. For example most reflex hammers are heavy, bulky instruments that physicians have to carry with them. Storing reflex hammers in pockets causes discomfort due to the odd shape and needed weight for reflex testing. For example, a common hatchet-type reflex hammer is made with a hatchet-like head connected to a ridged shaft. This type of reflex hammer, as well as others with shafts does not permit easy portability. Additionally reflex hammers can be inadvertently lost, misplaced or not handy when needed when not carried in pockets or lab coats. While it is known that a large population of physicians have used standard stethoscopes, alone, for reflex tests without this device, they have had limited success, due to the flex of the hose tubing, and some discomfort to the patient who has been contacted because of the hardness and shape of the stethoscope head.

U.S. Pat. No. 6,510,918 B2 (Bates) describes a combined stethoscope and reflex hammer, wherein the head of the reflex hammer is incorporated into an o-ring securing the diaphragm membrane of the stethoscope chest piece. A rigid handle is provided by a penholder rigidly affixed to the stethoscope in proximity to the chest piece. The reflex hammer of the present invention is attached to the stethoscope such that neither the diaphragm nor the bell of the stethoscope is affected by the reflex hammer.

European Patent No. 269,048 discloses a stethoscope modified to contain several medical devices, including a reflex hammer, attached laterally to the stethoscope head, a means for retaining a needle which commonly is used for neurological testing, and a light source. The light can be provided in the stethoscope body, grip or forkpiece joining the eartubes.

BRIEF SUMMARY OF THE INVENTION

The present invention is intended to provide a reflex hammer, which avoids the limitations, referred to above and further provide a hammer that is ideal for all normal neurological reflex testing. In the present invention the reflex hammer attaches to the distal end of a stethoscope. This has many advantages as it utilizes the existing weight of the stethoscope head. It attaches to the stethoscope in a way that does not impede the use of the stethoscope for normal pulmonary use. The shape of the hammerhead is mated to the stethoscope head in such a way that when combined the weight is equal to existing reflex hammers. The reflex hammer includes a light which can be switched on and off as needed for testing responses to light stimulation, and the combination device can eliminate the necessity of having to carry a separate light. Medical personnel can fold the stethoscope into their pocket, and/or drape it around their neck with no additional limitations.

Thus, one embodiment of the present invention is a tool for medical testing, the tool comprising, in combination:
a stethoscope, the stethoscope comprising:
a stethoscope head, the stethoscope head having an operational surface;
one or more earpieces; and
a means for connecting the stethoscope head with the earpiece;
a reflex hammer, the reflex hammer attached to the stethoscope head, the reflex hammer comprising:
a body having a rim, a wall adjoining the rim, and an opening therein, the stethoscope head being received in the opening, the rim being larger than the stethoscope head, the body positioned on the stethoscope head such that the reflex hammer does not interfere with the stethoscope head operational surface;
a handle, the handle joined to the body, the handle sized to receive and semi-rigidly receiving the connecting means therein; and
a light, the light retained within the body;
a switch in the body;
a power source within the body; and
the light being in electrical communication with the power source and the switch.

Another embodiment of the present invention is a method for employing a stethoscope as a neurological tool, comprising the steps of:
affixing to a stethoscope, the stethoscope comprising a stethoscope head having an operational surface;
one or more earpieces; and
a means for connecting the stethoscope head with the earpiece,
a reflex hammer, the reflex hammer comprising:
a body comprising two body members;
each body member including a notch at an end;
a light positioned between the body members and retained between the notches;
an opening within the first body member, the opening sized to receive and receiving a switch therein;
a receptacle for a power source within the second body member;
the light being in electrical communication with the power source and the switch;
the first body member comprising a means for engaging a handle;
a handle, the handle joined to the body, the handle comprising a pair of handle members, the handle sized to receive and semi-rigidly receiving the connecting means therein;
each handle member including an opening therethrough;
the first handle member further comprising an aperture therein; and a means for engaging the body;
positioning the body on the stethoscope head such that the reflex hammer does not interfere with the stethoscope head operational surface; and
positioning the handle so that the connecting means is semi-rigidly received therein.

Thus, the present invention comprises a tool for neurological and diagnostic testing comprises the combination of a stethoscope with a reflex hammer that includes a light. When mounted on the stethoscope head the reflex hammer extends beyond the head, without interfering with the normal use of the stethoscope. A handle, which may or may not be joined to the reflex hammer, is positioned on the flexible stethoscope tubing and provides a gripping surface for using the tool for neurological testing. The light enables the user to test responses to light. One embodiment has an opening between the reflex hammer body and the handle enabling the user to grasp and rotate the stethoscope head. The reflex hammer and light combination is adaptable for use with binaural and electronic stethoscopes, thus providing a convenient set of instruments within a single device. A detent on the handle provides an ergonomic grip, or a place for inclusion of indicia.

DESCRIPTION OF THE SEVERAL VIEWS OF THE DRAWINGS

The foregoing objects and advantages of the present invention will be more clearly understood when considered with the accompanying drawings, in which.

DETAILED DESCRIPTION OF THE INVENTION

The present invention is a medical device that can be used both as a stethoscope for the monitoring of bodily sounds, and as a reflex hammer with a built-in light for performing neurological testing, responses to light stimuli, and related functions.

Stethoscopes are well-known medical instruments, the "standard" (binaural) variety (FIGS. 1 and 2) being the most commonly known type. Stethoscopes enable the user to listen to respiratory and cardiac sounds within the chest, and for auscultation of the vascular or other sounds within the body. Newer, electronic stethoscopes have been developed which are stated to improve the user's ability to monitor these bodily sounds.

Figure 1:
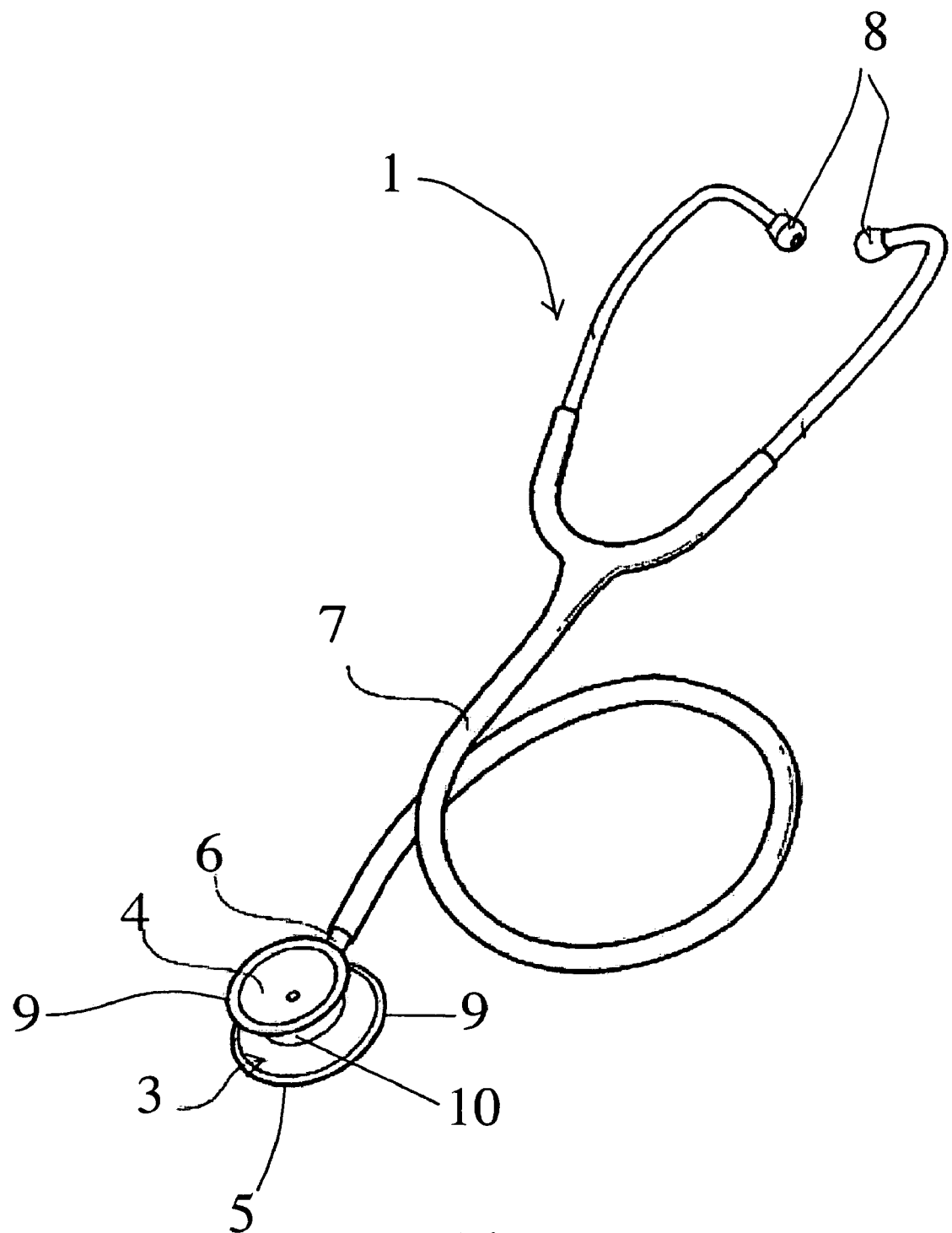
FIG. 1 is a perspective view of a "standard", binaural stethoscope.
Figure 2:
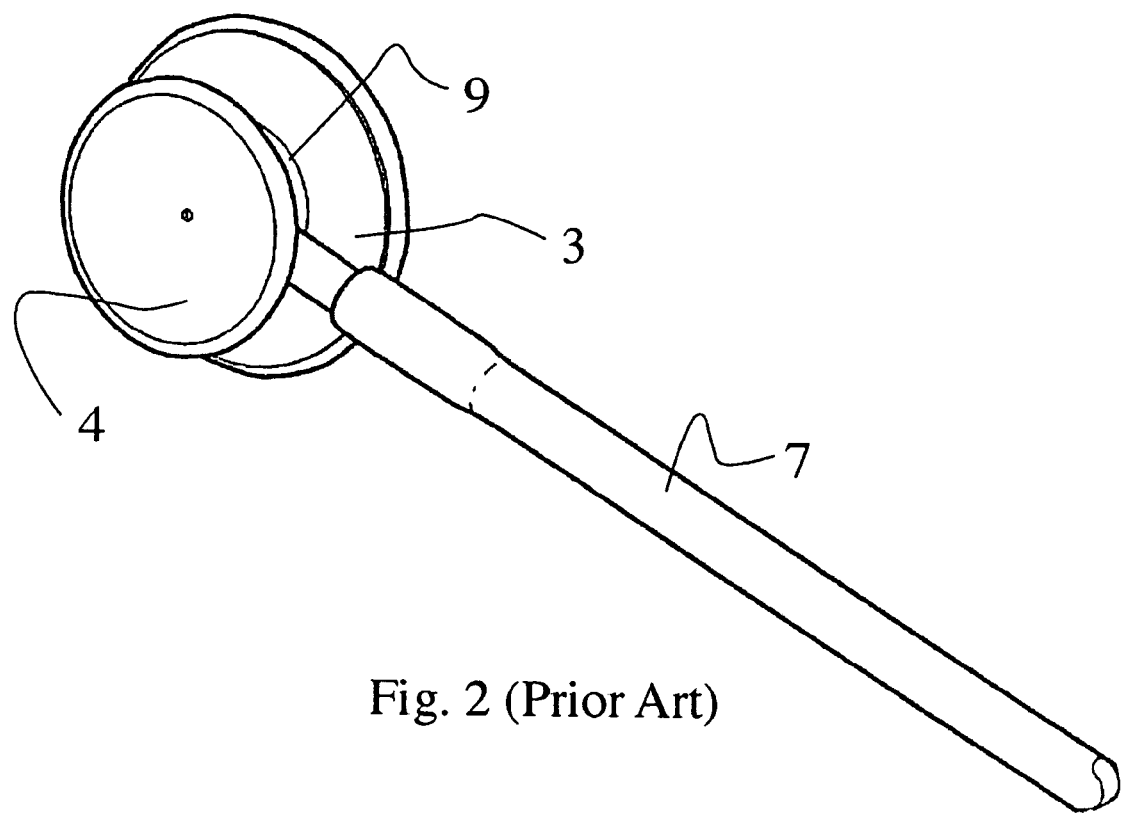
FIG. 2 is a close up view of a typical stethoscope head and tubing section.

Referring to the binaural stethoscope shown in FIG. 1, stethoscope 1 comprises a stethoscope head 3 having chest pieces 4 and 5, (chest pieces), a tubular stem 6 that extends from the stethoscope head 3 into a length of flexible tubing 7 that bifurcates and leads to two ear pieces 8, which are placed in the user's ears in order to listen to the sounds picked up by the operating surfaces 4 and 5. Surrounding chest pieces 4 and 5, along their outer edge, is a rim 9, which is generally manufactured from an elastomeric material, such as a rubber. The chest pieces are connected to each other by means of a neck 10, in communication with stem 6. By rotation of the stem 6, a user can switch between using the bell 4 and diaphragm 5.

For purposes of this specification, the terms "bell" and "diaphragm" will be used interchangeably with "chest pieces" and "operating surfaces" when referring to reference numerals 4 and 5, respectively.

Figure 3:
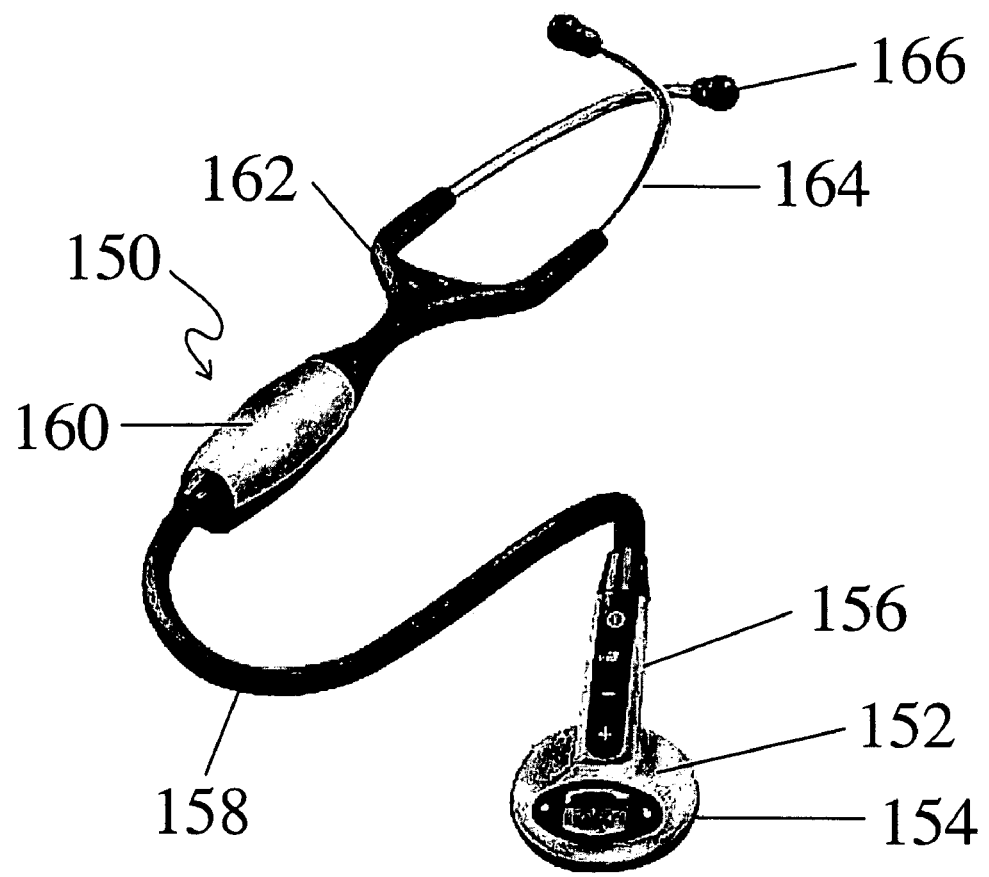
FIG. 3 is a perspective view of an electronic stethoscope.

Electronic stethoscopes generally resemble binaural ones, but the shapes of the head and diaphragm differ from those of a binaural stethoscope. Referring to FIG. 3, an electronic stethoscope 150 has a head 152 which includes a diaphragm 154. Head 154 is joined to tubing 158 by means of stem 156, in which some of the stethoscope electronics, such as volume controls, are contained. Module 160, mounted between lengths of tubing 158 and 162 also includes some of the stethoscopes electronics, such as a battery and battery chamber. The second length of tubing 162 bifurcates, and is joined to earpieces 166 by means of a connecting rod 164.

Figure 4A:
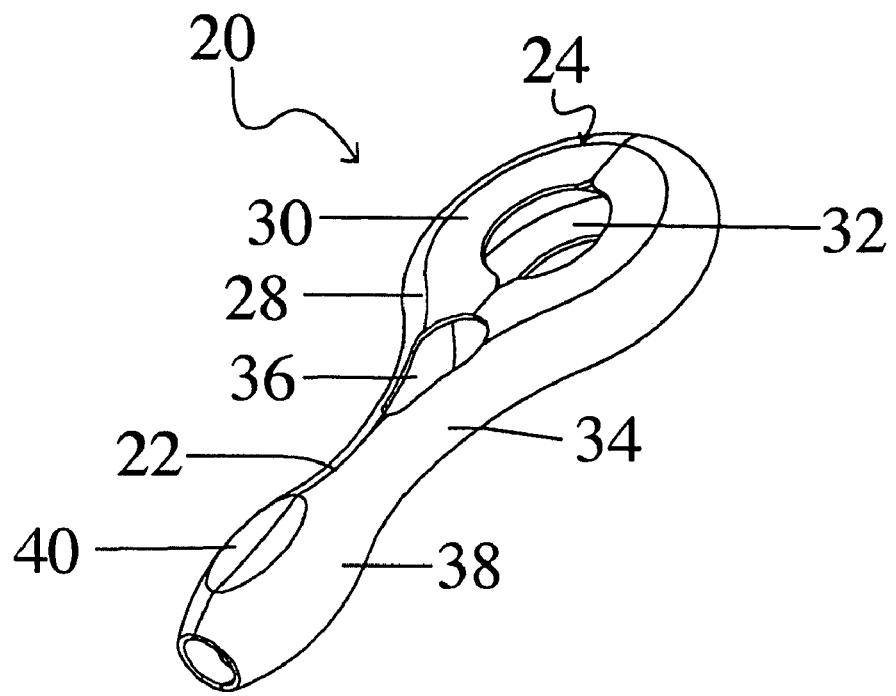
FIG. 4A is a perspective view of an embodiment of the present invention.
Figure 4B:
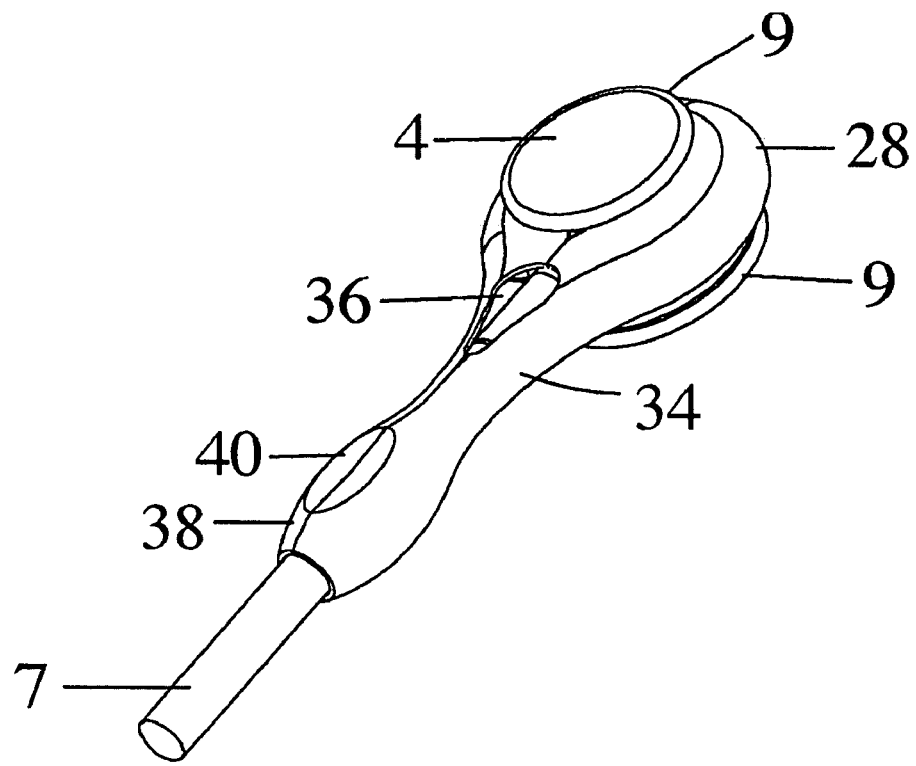
FIG. 4B is a perspective view of the embodiment of FIG. 4A attached to a stethoscope, a LITTMAN® (registered trademark of 3M Company Corp., St. Paul, Minn.) Classic II model stethoscope.

In accordance with one embodiment of the invention, a reflex hammer 20 is to be affixed to a stethoscope head 3 and tube section 7 (FIGS. 1, 4 and 5). One embodiment of the reflex hammer 20 of the present invention is illustrated in FIGS. 4 and 5.

The device 20 comprises a handle 22 that can be formed from one or more members, and a body 24 which engages the neck 10 between the chest pieces 4 and 5 (FIGS. 4 and 5). Handle 22 receives therein the stem 6 and a portion of the stethoscope tubing 7 creating a tool that is suitable for reflex testing (shown in FIG. 8). The combination of the handle 22 surrounding a portion of the stethoscope tubing 7, and the receipt of the stem 6 within the handle, creates what is termed a "semi-rigid" section, meaning that there is some flex to the combination, but much less flex than would occur in the absence of the handle (i.e., with just the tubing alone). The end 26 of the handle 22 can be used as a grip.

The body 24 comprises a rim 28 connecting a pair of walls 30. In this embodiment, body 24 is hollow, the opening 32 between the walls serving to receive therein the head of a stethoscope (for example, FIGS. 4B and 5A-5B). In the region 34 that forms a junction between the body 24 and the handle 22 is an aperture 36 into which the user can insert their fingers and rotate the stem 6 of the stethoscope. In another embodiment, the body can be solid, but still retain the opening for receipt of the stethoscope head.

In this embodiment, handle 22 includes a widened region 38 and a detent 40 towards the end of the handle, i.e., most distant from the body. This detent 40 can be formed on one or both sides of the handle 22 and, in this embodiment, the detent is generally flat, allowing for ergonomic finger placement and a comfortable grip.

Although not shown in the figures, the detents 40 may include other elements to improve the user's comfort, such as one or more ridges, nibs, pads, cushions, strips of tape, or similar elements known to those skilled in the art. The configuration of the detents 40 is such that indicia, such as, but limited to, a manufacturer's name, a logo, directions for use, advertising content, notations, or the like, could be placed thereon, using methods known to those skilled in the art.

Figure 8:
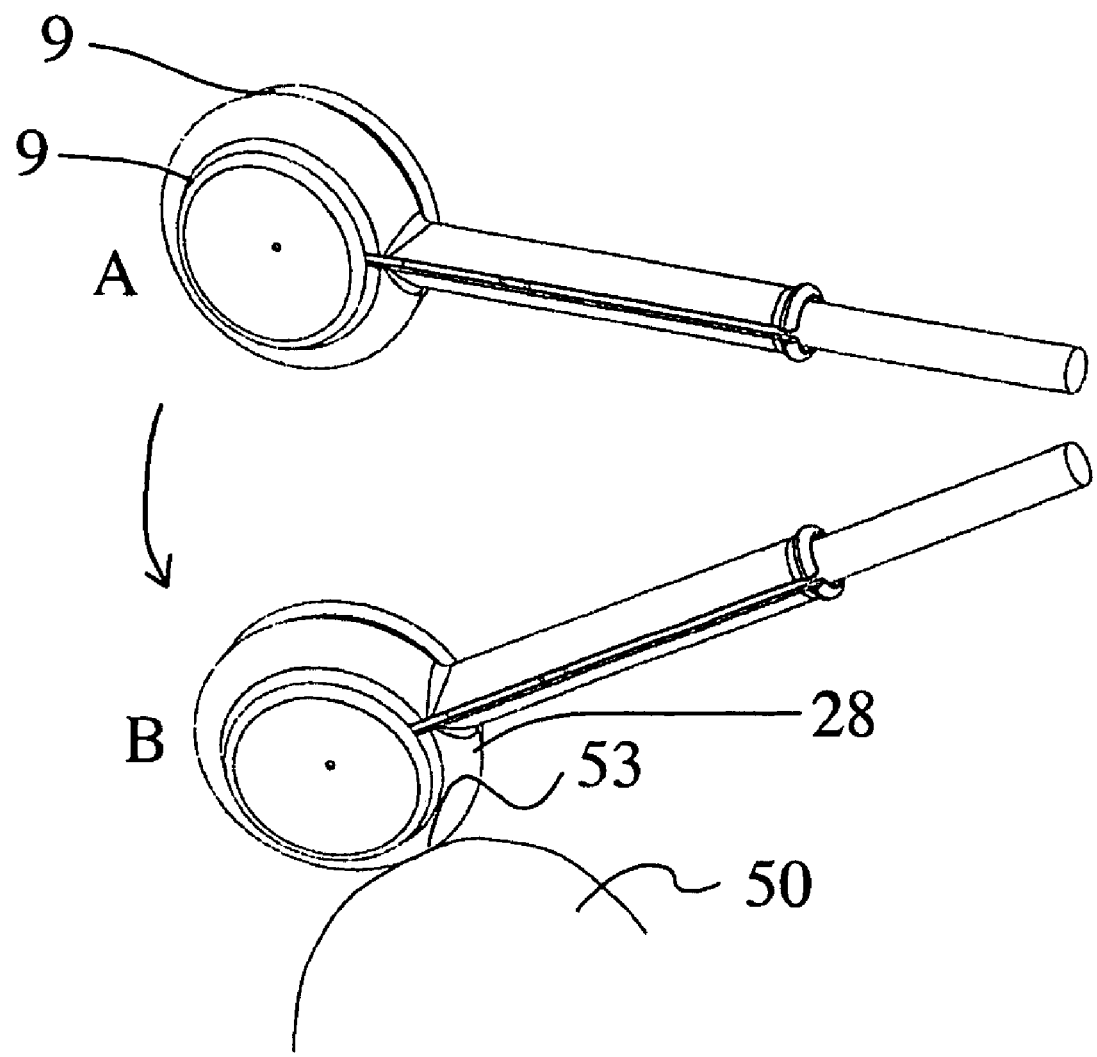
FIG. 8 illustrates schematic views of a reflex hammer embodying the present invention in actual usage when striking the knee of an individual.

The reflex hammer body 24 has a diameter that is larger than the stethoscope head 3 (see, for example, FIGS. 4B and 5B) thereby allowing the reflex hammer rim 28 to make contact with the larger surface area 53 of a patient (FIG. 8). The device may be secured to a range of different stethoscope tube thicknesses and head designs. A molded adapter may be provided to allow for the device to fit over a range of different stethoscopes, in accordance with an embodiment of the present invention.

The device may be slid over a portion of the tubular section 7 to form a tactile grip. The tactile grip allows the stethoscope head section to be gripped and used for various medical procedures. These procedures include, for example only and not intended as a limitation, reflex testing, percussion of a chest wall, or other bodily area in need of percussion for diagnostic purposes.

Figure 5A:
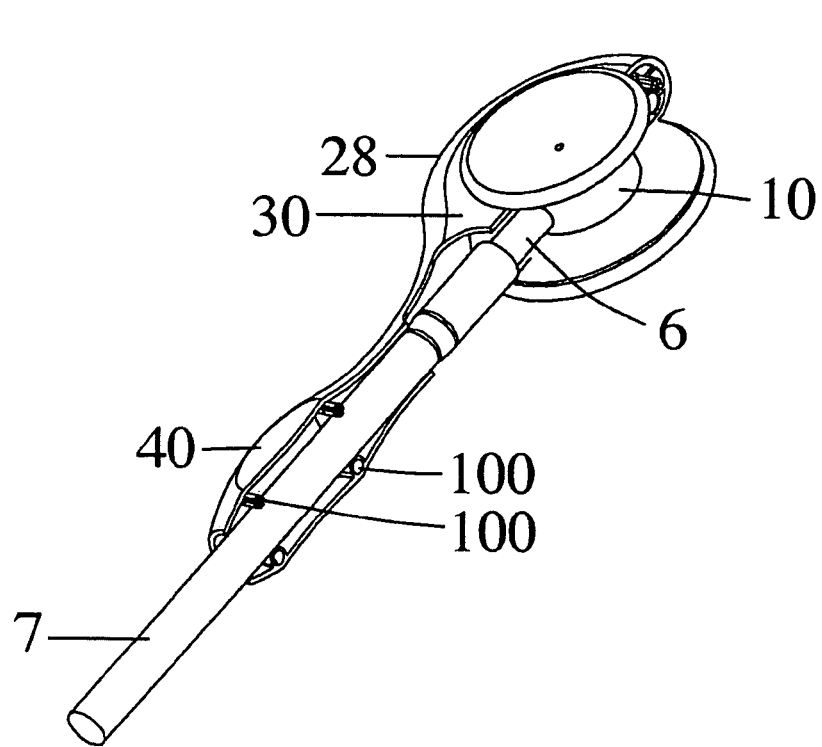
FIG. 5A is a cross-sectional view of the embodiment of FIG. 4A, taken along lines 5A-5A of FIG. 4A, attached to the stethoscope shown in FIG. 4B.
Figure 5B:
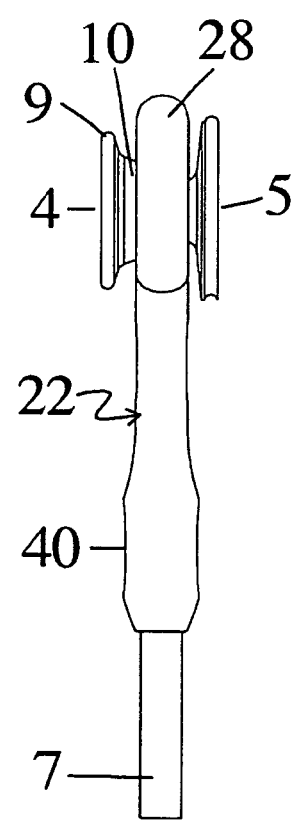
FIG. 5B is a side view of the embodiment shown in FIG. 4B.
Figure 6:
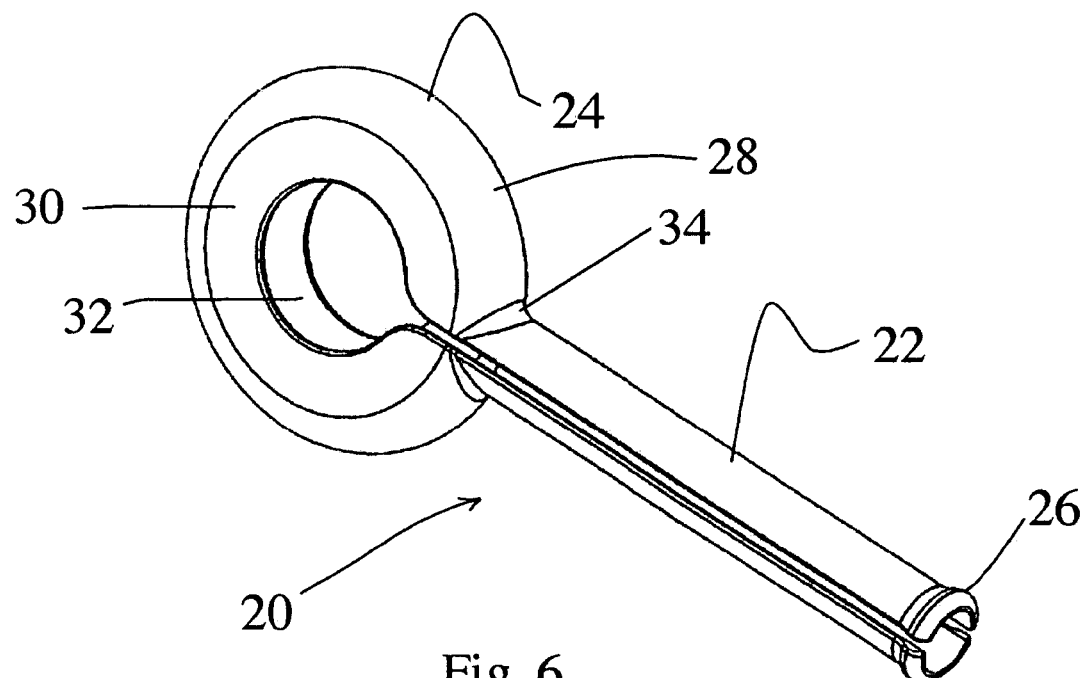
FIG. 6 is a perspective view of a reflex hammer in accordance with one embodiment of the present invention, prior to being affixed to a stethoscope head.
Figure 7:
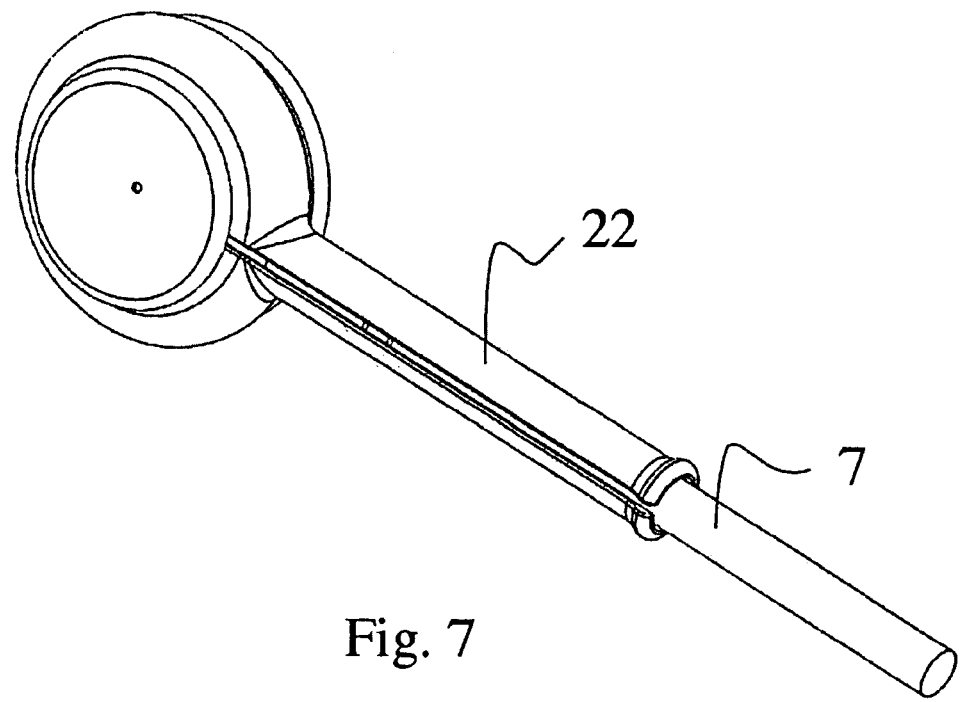
FIG. 7 is a perspective view of the reflex hammer affixed to the stethoscope, in accordance with an embodiment of the present invention.

FIG. 4 illustrates a method for attaching the reflex hammer 20 to a typical stethoscope. To this end, handle 22 is suitably secured to the tube 7 in a manner that allows the stethoscope dual head to rotate to its full 180 degrees to allow both the bell 4 and diaphragm 5 to be used (FIGS. 1, 5B).

Operation of the Device

The application of the reflex hammer 20 is illustrated in FIG. 8 where its movement relative to a reflex site, such as the knee 50 of a human, is shown. In use, two positions of the reflex hammer 20 as it is moved to an impact position are illustrated (omitting the hand of the person applying the hammer for purposes of illustration). In position A in FIG. 8, the reflex hammer 20 has begun its movement towards the knee 50. At position B, the reflex hammer has reached its point of impact 53 with the knee, to elicit a patellar tendon reflex, wherein the body 24 of reflex hammer strikes the patient. The reflex hammer 20 may be used in all ways as a typical reflex hammer is used. For example, it may be used in the percussion of a chest wall, or any other area of the body that may need to be percussed for diagnostic purposes.

ALTERNATE EMBODIMENTS

Alternate embodiments are shown in FIGS. 10 through 13, inclusive, which differ in the shape of the body and the handle of the reflex hammer 20.

Figure 9A:
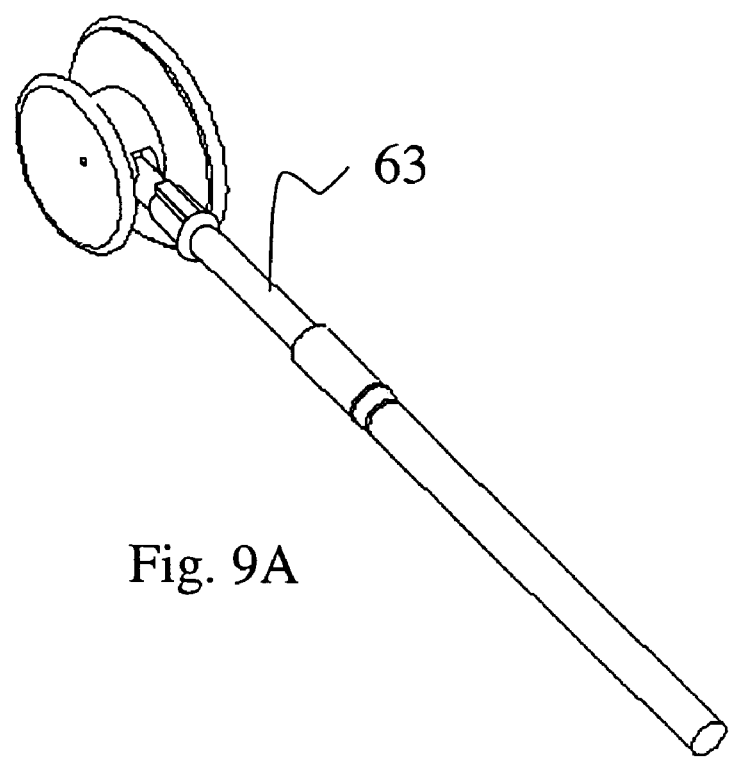
FIGS. 9A and B illustrate an adaptation in manufacturing, by increasing the length of the stem going into the stethoscope head, in accordance with one embodiment of the present invention.
Figure 9B:
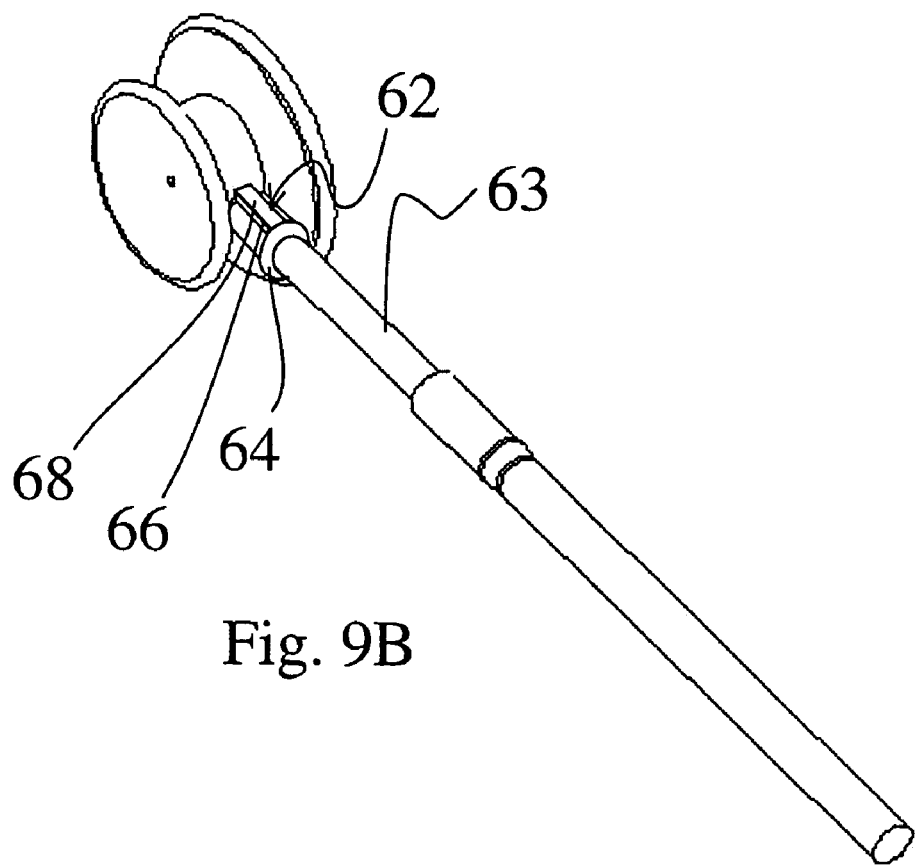
Figure 10:
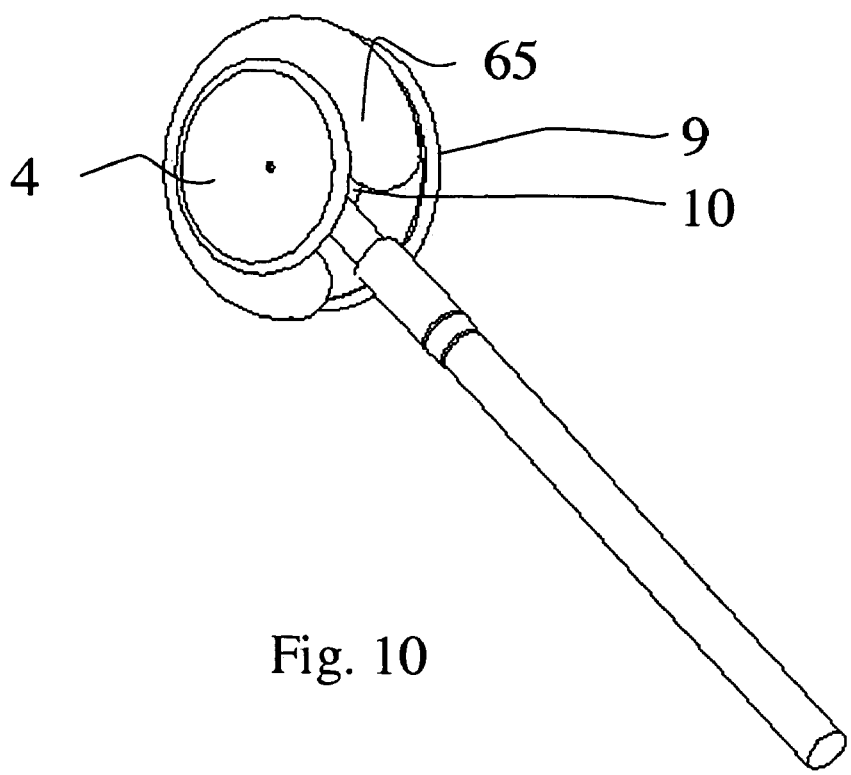
FIG. 10 shows a donut-shaped attachment element mounted on the head of the stethoscope to increase the surface area of the reflex striking force, in accordance with an embodiment of the present invention.

For example, if the length of the stem 6 of a stethoscope were to be increased (FIG. 9) from the "standard" lengths commonly employed in the industry, to form an elongated, or oversized (or extra-long) stem, thereby allowing a user to hold the stem as a reflex hammer, the present invention could be modified to suit such a stethoscope. For example, FIG. 10 shows a reflex hammer in the form of a donut-shaped attachment element 65 mounted on the head of the stethoscope to increase the surface area of the reflex striking force, in accordance with an embodiment of the present invention. In this embodiment, the user grasps the stem 6 to use the reflex hammer.

This attachment element 65 could be produced separately, by a manufacturer or an after-market device manufacturer, and could be made from a plastic or a rubber, or combinations thereof. This attachment element could be affixed to the stethoscope head 3 in one piece shaped like an incomplete circle, or in multiple pieces, or in symmetrical or asymmetrical shapes, where it could attach to the head around the neck 10, or around the bell 4 and/or diaphragm 5. Other embodiments anticipate increasing the striking area of the stethoscope head by either increasing the plastic/rubber or electrometric surface area or adding additional material to the stethoscope head. Instead of a donut-like configuration, this additional material could comprise a ring which would affix around the head of the stethoscope, and if made of an elastomeric or plastic material, provide shock absorbing properties as well. This ring could be affixed to the head 3 in one piece shaped like an incomplete circle, or in multiple pieces, or in symmetrical or asymmetrical shapes. It could attach to the head either around the diaphragm 5, bell aspect 4, or around the neck 10.

Further adaptations include a locking mechanism 62 that prevents the head from rotating without first releasing the lock. Such a locking mechanism could include mechanisms such as depressing a spring-loaded button through an aperture; twist-lock mechanisms, similar to those used on photographic tripods; click stop mechanisms; key lock mechanisms, or other locking mechanisms known to those skilled in the art. Such a locking mechanism could be built into the stethoscope before its initial sale, or can be designed to be retrofitted into existing stethoscopes. Similarly, a stethoscope could be modified with a telescoping device that would enable the elongation of the stem 6 to a distance similar to that of the handle 22 of an embodiment of the reflex hammer of the present invention. The distal aspect of the tubing 7 could also be made rigid by adding a stiffening attachment to the stem 6. This elongated stem or stiffened section would act as a handle for the reflex hammer function of the stethoscope. The locking mechanism 62 would also lock the head 3 on its axis so that the head does not shift or rotate upon striking. The locking mechanism could be incorporated into the stem or be affixed to the axis from outside of the rotational mechanism.

Figure 11:
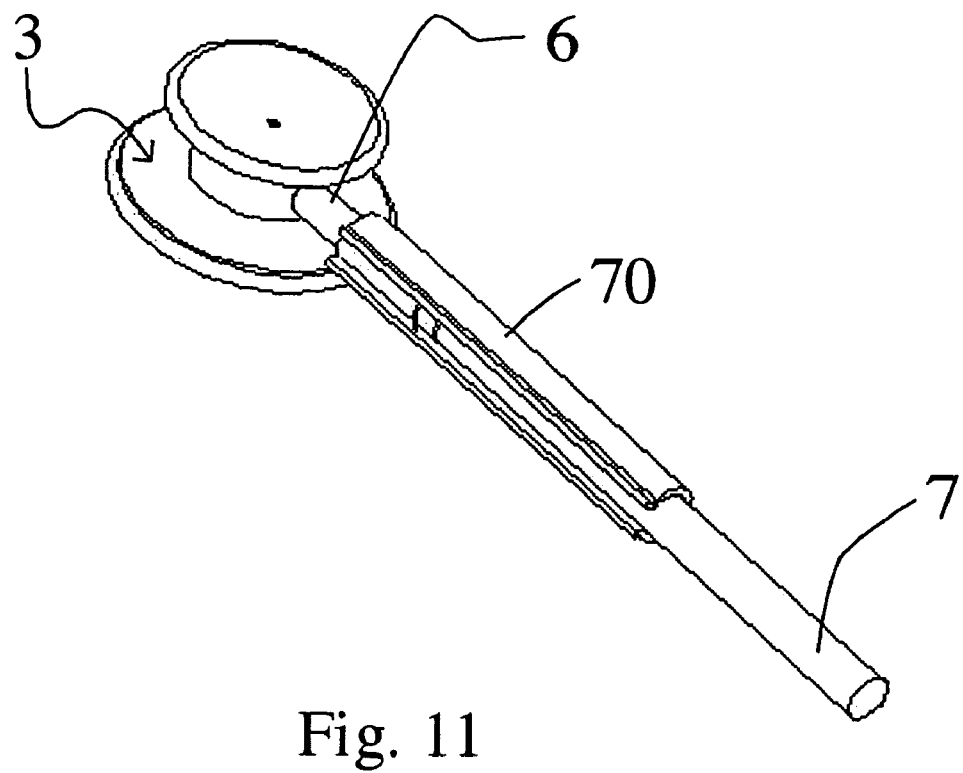
FIG. 11 shows an add-on stem that would allow a stethoscope head to function as a reflex hammer, in accordance with an embodiment of the present invention.

FIG. 11 illustrates an embodiment in which the distal aspect of the tubing 7 has been made rigid by adding a stiffening attachment 70 to the stem 6. Stiffening element 70 is an add-on extension, or tube, made from a material such as a plastic or metal, and once mounted on this region of tubing 7, limits the flex of the distal end of the stethoscope tubing 7. This elongated stem or stiffened section acts as a handle for the reflex hammer function of the stethoscope. As will be described further, stiffening element 70 can fit over the tubing in a variety of ways such as: a "clam shell" design thereby clipping over the tubing, but not compressing it. It could lock in this position or could be easily removed. The design consists of a rigid tube with a slit longitudinally allowing for the tubing to be compressed into the rigid tube and then exist therein in an uncompressed fashion. This tube could extend until it reached the median aspect of the head 3 or extend any distance including the possible extension to attach or cover some aspect of the head. It could involve a flange that would extend to the head and stabilize it to stop it from rotating on its axis.

Figure 12:
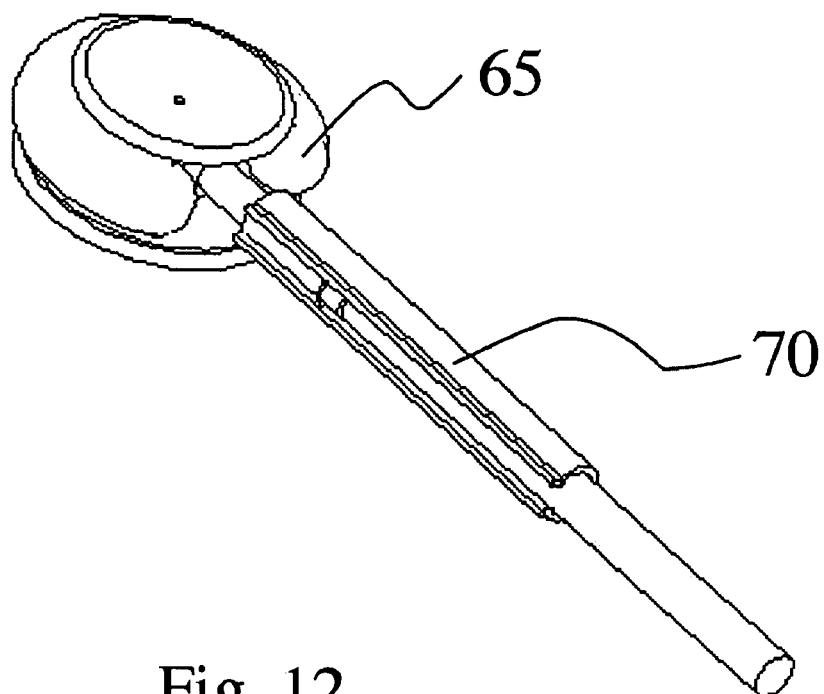
FIG. 12 illustrates both the donut-shaped attachment element and the add-on stem, attached to a stethoscope, in accordance with an embodiment of the present invention.

FIG. 12 illustrates the combination comprising both the donut-shaped attachment element 65 and the add-on stem 70 attached to a stethoscope, to act as a reflex hammer, in accordance with another embodiment of the present invention.

Figure 13:
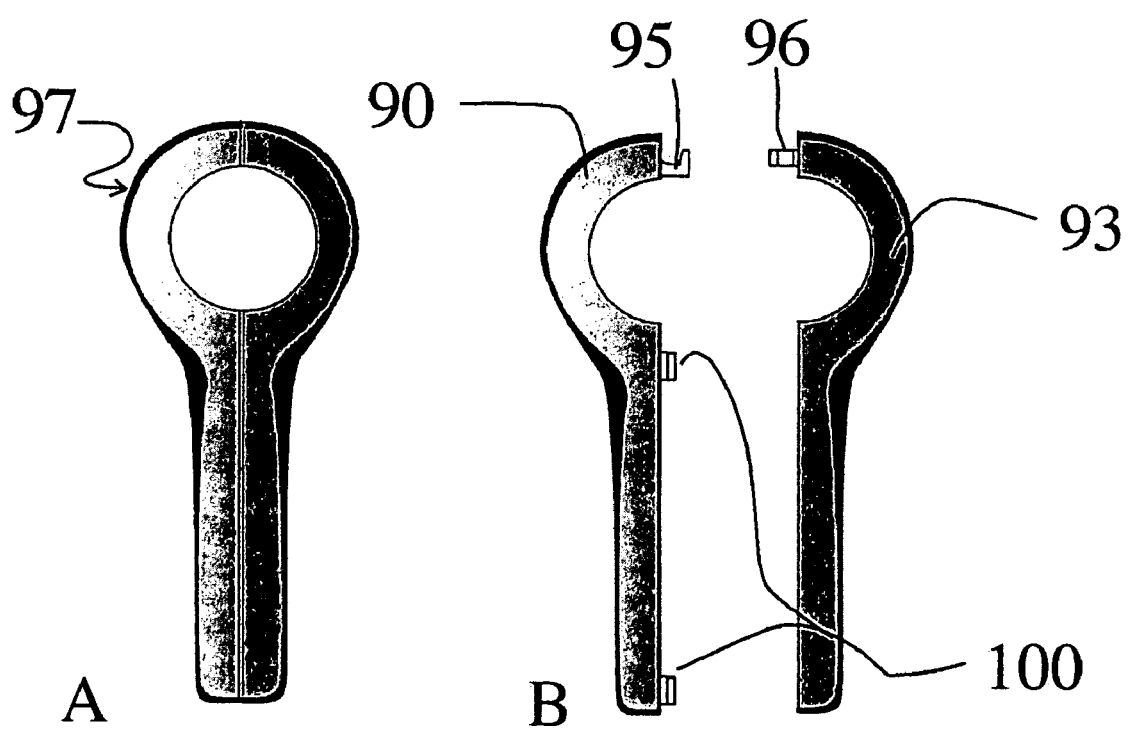
FIGS. 13A and B illustrate an embodiment of the reflex hammer manufactured as a two-piece clam shell that can snap together around a stethoscope head.

FIG. 13 shows another alternative embodiment 97 that is manufactured in a two-piece manner. The two members 90 and 93 are symmetrical, and designed to interlock with each other to form reflex hammer 97. Each member 90 and 93 contains one or more fastening means, which could be a hook and eye closure 95 and 96, respectively. The fastener could also be a snap 98 or other fastener 100, known to those skilled in the art, such as, but not intended to be limited to, a locking pin, button, nib, adhesive strips, hook and loop fasteners or the like. Alternatively, the members could contain ridges or similar means to enable them to be joined by means of a press-fit or snap-fit. The fasteners could be permanently affixed to each other or be removable depending on manufacturing method. The parts would snap, glue or fasten together in such a way that they become one piece 97 and would be able to rotate freely around the stethoscope hose. As can be seen in FIG. 5A, the location of the fasteners 100 within the reflex hammer handle are spaced sufficiently far apart to act as a means for retaining the stethoscope tubing 7 therein, and can also function as a guide for attaching the reflex hammer of the present invention to a stethoscope.

Figure 14:
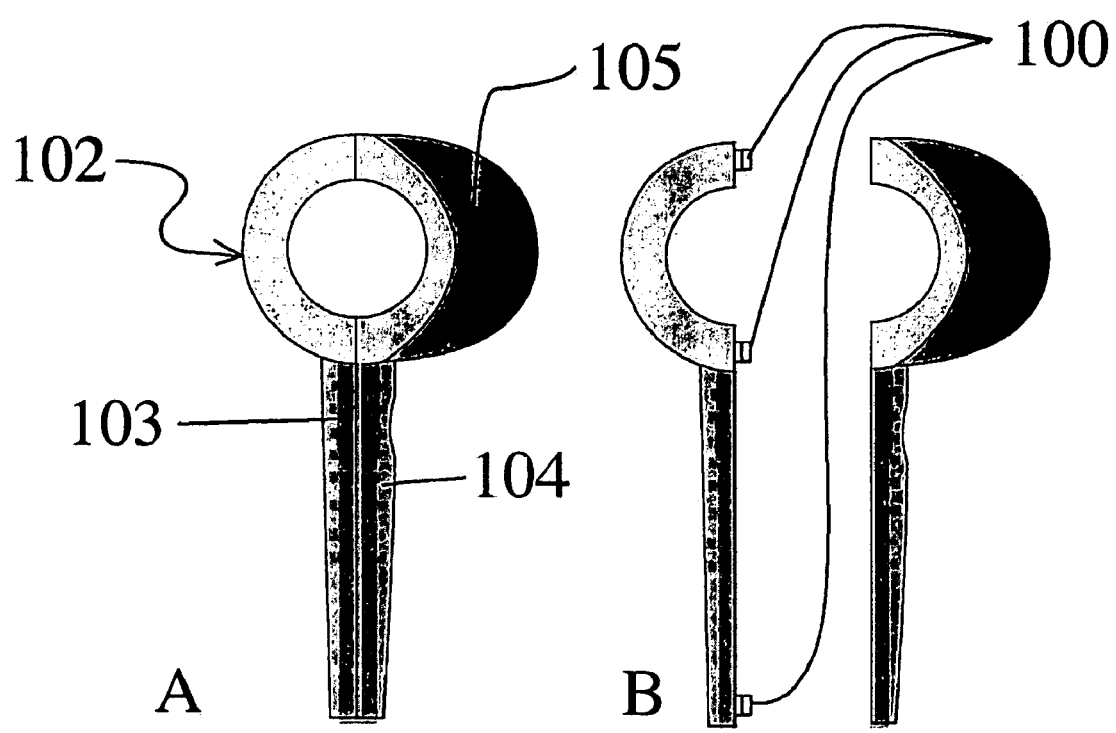
FIGS. 14A and B illustrate another embodiment of the reflex hammer manufactured as a two-piece asymmetrical clam shell that can be snapped together around the stethoscope head.

FIG. 14 shows an asymmetrical version 102 of another alternative embodiment. In this embodiment, the parts would snap, glue or fasten together in such a way that the hose could be able to rotate freely if desired. The parts could either be permanently affixed to each other of removable, depending on manufacturing method. Additionally the head of the members 103, 104 could be asymmetrical, allowing for different striking surface areas 105. The striking area 105 could be molded in the similar plastic as the clamshell or in a different durometer material either molded in or affixed secondarily in assembly. Additionally the parts could snap together by means of fasteners 110, such as a button, pin, nib, press-fit or snap-fit, or other fastener as has been described previously.

Figure 15:
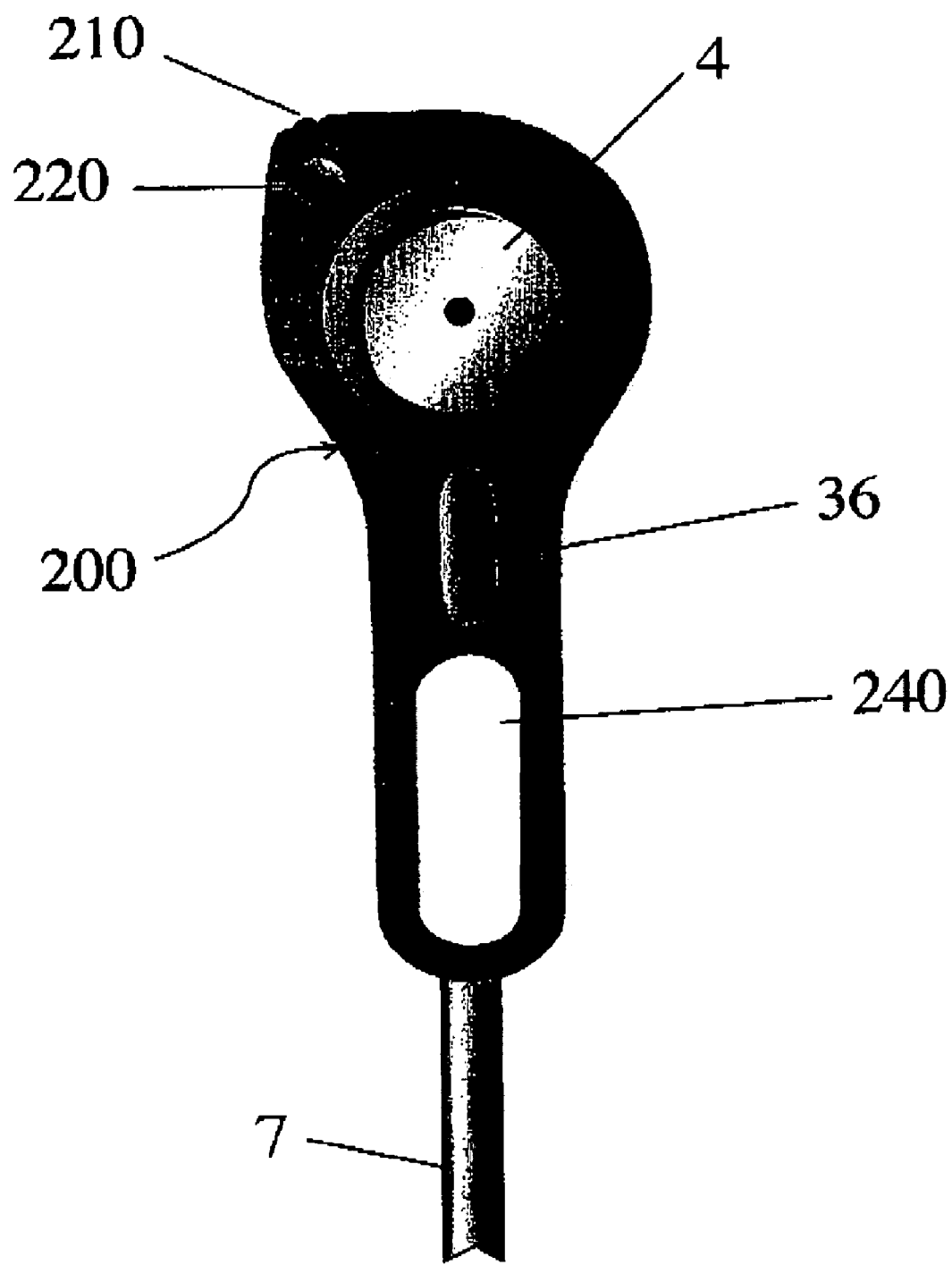
FIG. 15 is a perspective view of another embodiment of the reflex hammer, in which a light has been incorporated into the reflex hammer.
Figure 16:
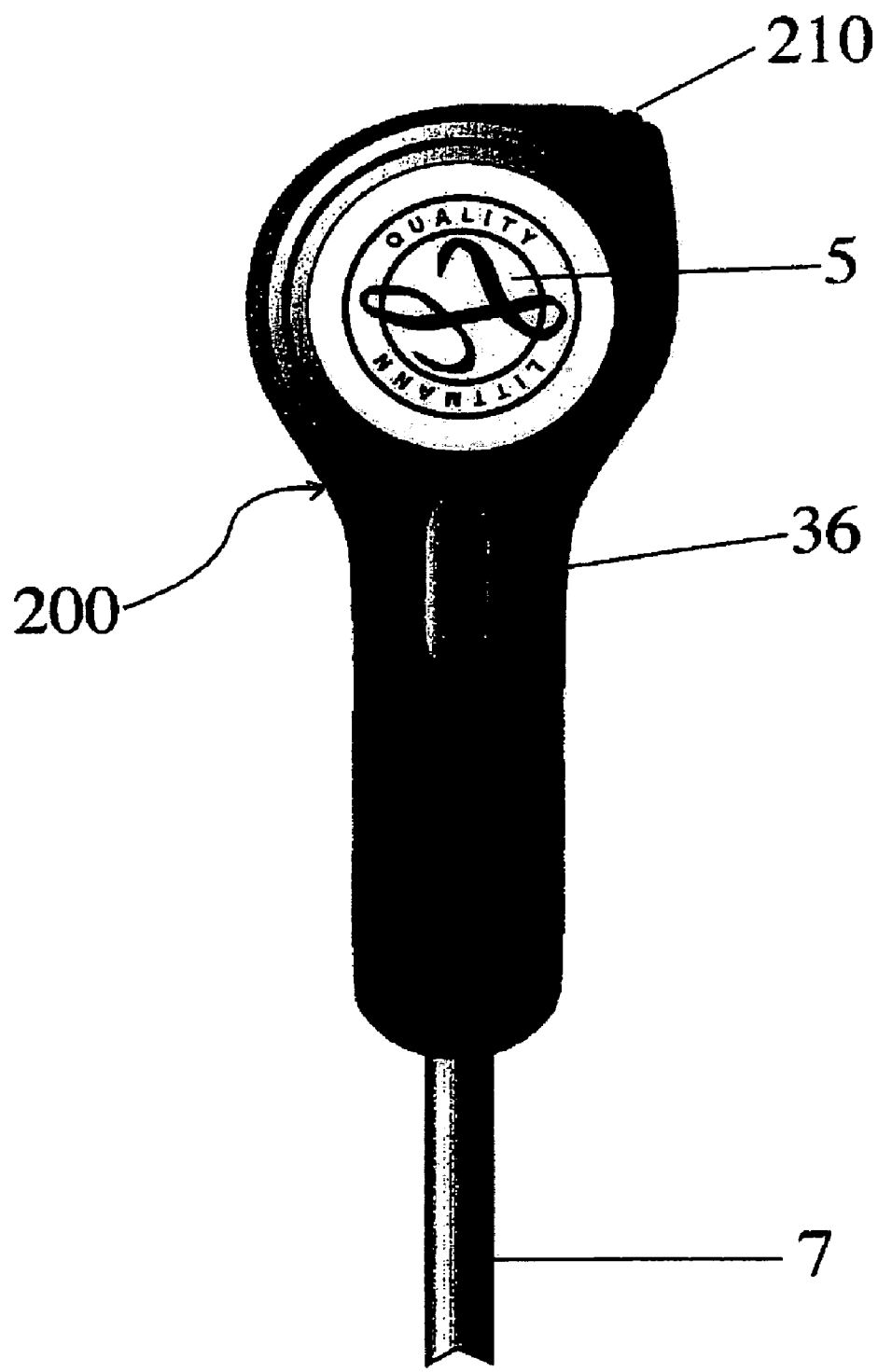
FIG. 16 is a perspective view of the embodiment shown in FIG. 15.
Figure 17:
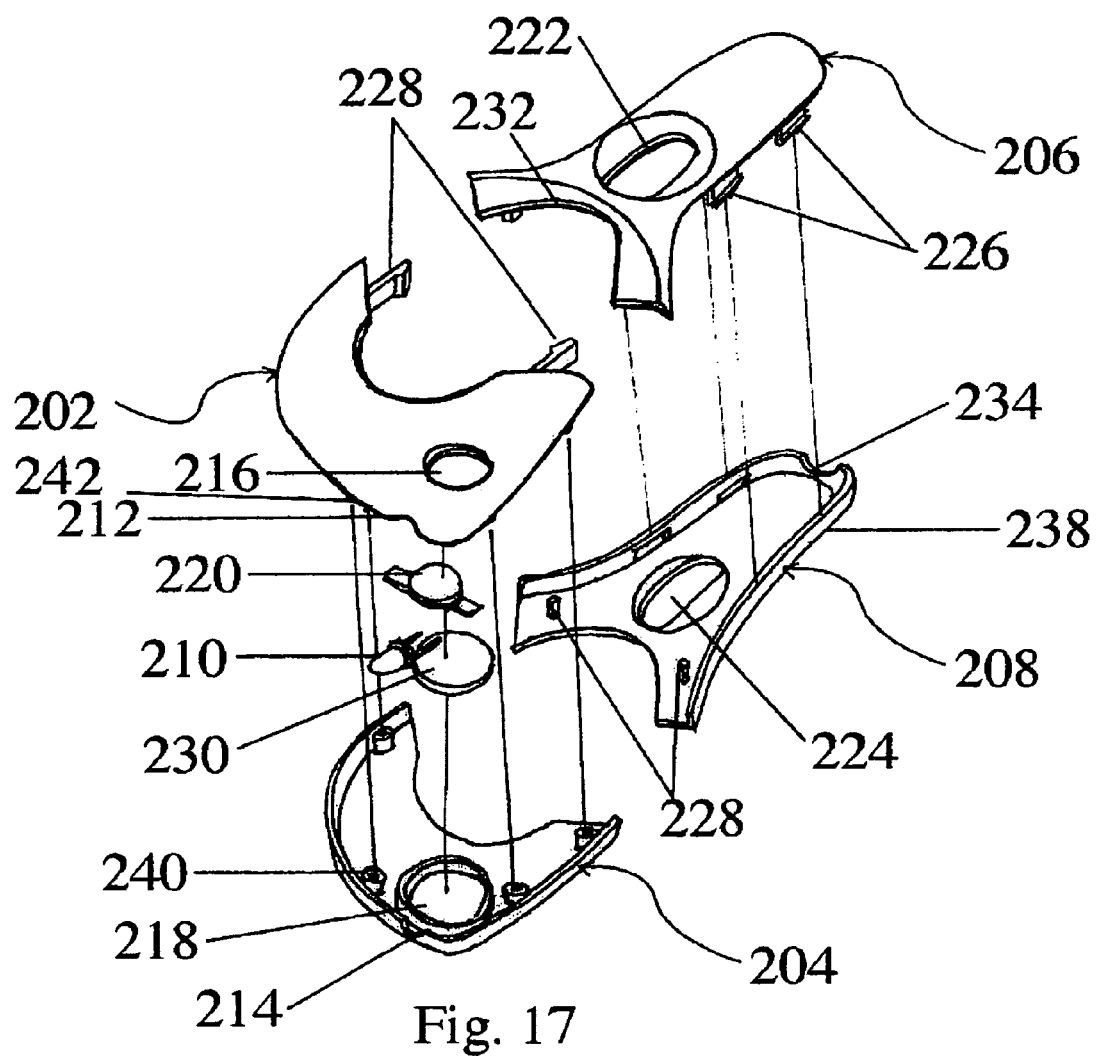
FIG. 17 is an exploded view of the embodiment shown in FIG. 16, and is a multi-piece shell that fits around the stethoscope head.

FIGS. 15 through 17 illustrate another embodiment 200 that includes a light 210 incorporated into the hammer. This embodiment is manufactured using four main pieces, including two head members 202, and 204, and two handle members 206 and 208. As seen in FIG. 17, first head member 202 includes a notch 212, an opening 216, and a pair of prongs 228 which are received in handle member 206. A switch 220 is received within opening 216, and the switch 220 is in electrical communication with light 210 and battery 230, the battery being in the form of a button type cell, although other types and sizes of batteries could be employed in alternative embodiments. Alternatively, another power source, such as a photovoltaic (or solar) cell, could be used, provided the head member includes a means for permitting light to reach such a photovoltaic cell, such as a window or other opening in the head member. Battery 230 is positioned within battery holder 218, which is formed within the second head member 204. The circuitry connecting the power source 230, the light 210, and the switch 230 are conventional components, and are not shown. Second head member 204 includes a notch 214, the notches 212 and 214 being sized to fit around the light, and retain the light therein. Light 210 can be an incandescent bulb of the type used in various types and sizes of flashlights, a halogen bulb, a xenon light bulb, a light emitting diode ("LED"), other type of bulb or light source which may be suitable for use in determining a response to a light stimulus. The head members 202 and 204 fit together by means of a press fit to form the head of the reflex hammer.

Second handle member 208 includes an opening 224 therein, and a slot 234 through which the stethoscope hose 7 will pass when the reflex hammer is being attached to a stethoscope. A pair of clips 226 are positioned along one wall 238 of the second handle member 208, and a pair of prongs 228 are mounted on the inside surface of second handle member 208 which will receive a mating component of first handle member 206. The structure of first handle member 206 is similar to that of the second handle member 208. First handle member lacks the prongs 228. The clips 226 on first handle member are designed to engage the wall 238 of second handle member 208. First handle member 206 includes an opening 222 therein, the openings 222, 224 and 234 providing the user access to the stem of the stethoscope in order to change the operative stethoscope surface. A slot 236 in both handle members provides the user access to the stethoscope (see FIG. 15). When the device is assembled on a stethoscope, the handle members 206 and 208 fit over the stethoscope hose 7, the clips and prongs of opposing head and handle members are engaged at an appropriate position to retain the device on the stethoscope, and the clips 226 engage and retain an opposite wall of the opposing handle member.

When assembled, the head assembly, including the two head members 202, and 204, the power source 230, light 210, electronics and switch 220, is assembled as one piece. The head assembly is then placed over the stethoscope head 4 and held together via prongs and mating components 242 to attach it to the snapped together handle assembly. The switch 220 could be placed anywhere on the hammer 200. Pressing down on the switch activates the light. This embodiment could also have an area for indicia such as branding and/or custom labeling 240. Although a light is mounted within this particular embodiment, it is to be understood that a light, switch, power source and electrical circuitry can also be fitted within the various embodiments illustrated in this specification, although with slightly different configurations and arrangement of parts. Those skilled in the art will recognize that this device can be assembled in alternate means and varying numbers of segments, provided that the assembled parts can be attached around the stethoscope.

In an embodiment of the present invention, the reflex hammer 20, or 200, is made of a plastic material, but any suitable material could be employed, including natural or synthetic rubbers, metals, polytetrafluoroethylene (TEFLON®, DuPont Corp. Wilmington Del.), nylon, other plastics, such as polyethylene, polycarbonate, polypropylene, polyvinyl carbonate, or the like could be substituted therefor.

Therefore, although this invention has been described with a certain degree of particularity, it is to be understood that the present disclosure has been made only by way of illustration and that numerous changes in the details of construction and arrangement of parts may be resorted to without departing from the spirit and scope of the invention.

We claim:

1. A tool for medical testing, the tool comprising, in combination:
    a stethoscope, the stethoscope comprising:
        a stethoscope head, the stethoscope head having an operational surface;
        one or more earpieces; and
        a means for connecting the stethoscope head with the earpiece;
    a reflex hammer, the reflex hammer attached to the stethoscope head, the reflex hammer comprising:
        a body having a rim, a wall adjoining the rim, and an opening therein, the stethoscope head being received in the opening, the rim being larger than the stethoscope head, the body positioned on the stethoscope head such that the reflex hammer does not Interfere with the stethoscope head operational surface;
        a handle, the handle joined to the body, the handle sized to receive and semi-rigidly receiving the connecting means therein; and
        a light, the light retained within the body;
        a switch in the body;
        a power source within the body; and
        the light being in electrical communication with the power source and the switch.

2. The tool as described in claim 1, wherein the stethoscope is a binaural stethoscope.

3. The tool as described in claim 1, wherein the stethoscope is an electronic stethoscope.

4. The tool as described in claim 1, wherein the stethoscope further comprises a means for selecting the stethoscope head operational surfaces, the means for selecting the stethoscope head operational surfaces being between the stethoscope head and the means for connecting.

5. The tool as described in claim 4, wherein the reflex hammer further comprises an opening therein, the opening in the body being between the rim and the handle, the opening allowing access to the means for selecting the stethoscope head operational surfaces.

6. The tool as described in claim 5, wherein the handle further comprises a detent.

7. The tool as described in claim 6, wherein the detent is distal to the stethoscope head.

8. The tool as described in claim 5, further comprising a means for locking the means for selecting the stethoscope head operational surface.

9. The tool as described in claim 6, wherein the body further comprises a pair of joined members.

10. The tool as described in claim 9, wherein the members are not symmetrical.

11. The tool as described in claim 10, wherein the members are joined by a fastener.

12. The tool as described in claim 11, wherein the fastener is selected from the group consisting of hook and eye closures, prongs and mating components, hook and loop fasteners, snaps, buttons, ridges, press-fit and snap-fit components.

13. The tool as described in claim 7, wherein the medical testing is selected from the group consisting of neurological testing, responses to light stimulations, reflex testing, percussion of an abdomen, percussion of a thorax, and percussion of a body part in need of percussion.

14. A method for employing a stethoscope as a diagnostic tool, comprising the steps of:
    affixing to a stethoscope, the stethoscope comprising a stethoscope head having an operational surface;
    one or more earpieces; and
    a means for connecting the stethoscope head with the earpiece,
    a reflex hammer, the reflex hammer comprising:
        a body comprising two body members;
        each body member including a notch at an end;
        a light positioned between the body members and retained between the notches;
        an opening within the first body member, the opening sized to receive and receiving a switch therein;
        a receptacle for a power source within the second body member;
        the light being in electrical communication with the power source and the switch;
        the first body member comprising a means for engaging a handle;
        a handle, the handle joined to the body, the handle comprising a pair of handle members, the handle sized to receive and semi-rigidly receiving the connecting means therein;
        each handle member including an opening therethrough;
        the first handle member further comprising an aperture therein; and a means for engaging the body;
    positioning the body on the stethoscope head such that the reflex hammer does not interfere with the stethoscope head operational surface; and
    positioning the handle so that the connecting means is semi-rigidly received therein.

15. The method as described in claim 14, further comprising the step of actuating the switch to turn on the light, and determining the response of a patient to the light.

16. The method as described in claim 15, further comprising the step of contacting the patient with the rim of the reflex hammer.

17. A device to convert a stethoscope into a tool for medical testing, wherein the stethoscope comprises a stethoscope head, the stethoscope head having an operational surface; one or more earpieces, and a means for connecting the stethoscope head with the earpiece; the device comprising:
    a reflex hammer for attachment to the stethoscope head, the reflex hammer comprising:
    a body comprising two body members;
        each body member including a notch at an end,
        a light positioned between the body members and retained between the notches;
        an opening within the first body member, the opening sized to receive and receiving a switch therein;
        a receptacle for a power source within the second body member, the light being in electrical communication with the power source and the switch;
        the first body member comprising a means for engaging a handle;
        a handle, the handle joined to the body, the handle comprising a pair of handle members, the handle sized to receive and semi-rigidly receiving the connecting means therein;

each handle member including an opening therethrough, the first handle member further comprising an aperture therein, and a means for engaging the body, and the stethoscope head being received between the body members and the handle members, the body being larger than the stethoscope head, the body positioned on the stethoscope head such that the reflex hammer does not interfere with the stethoscope head operational surface.

18. The device as described in claim 17, wherein the means for engaging comprises a prong, a first prong extending from the first body member and a mating component extending from the first handle member.

19. The device as described in claim 18, wherein the handle members further comprise a clip, and wherein the handle members are joined by the clips.

20. A tool for medical testing, the tool comprising, in combination:

a stethoscope, the stethoscope comprising:
  a stethoscope head, the stethoscope head having an operational surface;
  one or more earpieces; and
  a means for connecting the stethoscope head with the earpiece;

a reflex hammer, the reflex hammer attached to the stethoscope head, the reflex hammer comprising:
  a body having two body members, each body member including a notch at an end,
  a light positioned between the body members and retained between the notches;
  an opening within the first body member, the opening sized to receive and receiving a switch therein;
  a receptacle for a power source within the second body member, the light being in electrical communication with the power source and the switch;
  the first body member further comprising a prong;
  the body members being joined by means of a press fit; and
  a handle, the handle joined to the body, the handle sized to receive and semi-rigidly receiving the connecting means therein; the handle further comprising a pair of handle members, each handle member including an opening therethrough,
  the first handle member further comprising an aperture therein, and a prong, the prong engaging a mating component of the first body member when the body is joined to the handle, and
  the stethoscope head being received between the body members and the handle members, the body being larger than the stethoscope head, the body positioned on the stethoscope head such that the reflex hammer does not interfere with the stethoscope head operational surface.

21. The tool as described in claim 20, wherein the stethoscope is chosen from the group consisting of binaural stethoscopes and electronic stethoscopes.

22. The tool as described in claim 21, wherein the stethoscope further comprises a means for selecting the stethoscope head operational surface, the means for selecting the stethoscope head operational surfaces being between the stethoscope head and the means for connecting.

* * * * *